(12) United States Patent  (10) Patent No.: US 9,157,903 B2
Seifried et al.  (45) Date of Patent: Oct. 13, 2015

(54) MICROFLUIDIC SEPARATION OF PLASMA FOR COLORMETRIC ASSAY

(75) Inventors: Lynn Seifried, Minneapolis, MN (US); Ron Bardell, St. Louis Park, MN (US)

(73) Assignee: Honeywell International Inc., Morristown, NJ (US)

( * ) Notice: Subject to any disclaimer, the term of this patent is extended or adjusted under 35 U.S.C. 154(b) by 836 days.

(21) Appl. No.: 13/398,683

(22) Filed: Feb. 16, 2012

(65) Prior Publication Data

US 2012/0220047 A1 Aug. 30, 2012

Related U.S. Application Data

(60) Provisional application No. 61/446,924, filed on Feb. 25, 2011.

(51) Int. Cl.
| | |
|---|---|
| *G01N 1/18* | (2006.01) |
| *G01N 33/49* | (2006.01) |
| *B01L 3/00* | (2006.01) |
| *G01N 1/28* | (2006.01) |
| *G01N 1/34* | (2006.01) |

(52) U.S. Cl.
CPC ........ *G01N 33/491* (2013.01); *B01L 3/502753* (2013.01); *B01L 2200/0647* (2013.01); *B01L 2300/0681* (2013.01); *B01L 2300/0867* (2013.01); *B01L 2400/0481* (2013.01); *G01N 1/28* (2013.01); *G01N 1/34* (2013.01); *Y10T 436/255* (2015.01)

(58) Field of Classification Search
CPC ..... G01N 33/491; G01N 33/483; G01N 1/28; G01N 1/34; B01L 3/502753; B01L 3/50273; B01L 3/502738; B01L 2200/0647; B01L 2300/0681; B01L 2300/0867; B01L 2300/087; B01L 2300/0864; B01L 2400/0481; B01L 2400/0487; B01L 2400/049
See application file for complete search history.

(56) References Cited

U.S. PATENT DOCUMENTS

| | | | |
|---|---|---|---|
| 3,799,742 A | 3/1974 | Coleman | |
| 4,761,381 A * | 8/1988 | Blatt et al. | ..................... 436/165 |
| 6,656,428 B1 * | 12/2003 | Bickoff et al. | ................ 422/404 |
| 7,641,862 B2 | 1/2010 | Noetzel et al. | |

(Continued)

FOREIGN PATENT DOCUMENTS

| | | |
|---|---|---|
| CN | 1653323 A | 8/2005 |
| CN | 101133324 A | 2/2008 |

OTHER PUBLICATIONS

"European Application Serial No. 12156773.9, Response filed Nov. 13, 2012 to Office Action mailed Jul. 13, 2012", 11 pgs.

(Continued)

*Primary Examiner* — Christopher A Hixson
(74) *Attorney, Agent, or Firm* — Schwegman Lundberg & Woessner, P.A.

(57) ABSTRACT

A device includes a plasma separation membrane, a capillary channel positioned adjacent the plasma separation membrane to receive plasma from blood placed on the plasma separation membrane, at least one cuvette coupled to the capillary channel, a gas permeable membrane, and a distribution channel coupled to the capillary channel to provide plasma to the cuvette, wherein the cuvette is configured to hold an amount of plasma with reagent suitable for colorimetric assay by a tester to hold the device. Variations include the use of a quantitation channel to provide a selected amount of plasma and a mixing channel to mix plasma with a diluent.

20 Claims, 4 Drawing Sheets

(56) References Cited

U.S. PATENT DOCUMENTS

2001/0035351 A1* 11/2001 Simpson et al. ............ 204/453
2005/0106066 A1    5/2005 Saltsman et al.
2006/0228259 A1   10/2006 Samsoondar
2007/0183935 A1*  8/2007 Clemmens et al. .......... 422/100

OTHER PUBLICATIONS

"European Application Serial No. 12156773.9, European Search Report mailed Jun. 27, 2012", 3 pgs.

"European Application Serial No. 12156773.9, Office Action mailed Jul. 13, 2012", 6 pgs.

"European Application Serial No. 13176894.7, Office Action mailed Oct. 23, 2013", 5 pgs.

"European Application Serial No. 13176894.7, Response filed Apr. 22, 2014 to Office Action mailed Oct. 23, 2013", 8 pgs.

"Chinese Application Serial No. 201210105716.9, Office Action mailed Apr. 24, 2015", (w/ English Translation), 24 pgs.

Shim, Joon S. et al., "An on-chip whole blood plasma separator with bead-packed microchannel on COC polymer", *Biomed Microdevice*, 12(5), (2010), 949-957.

Tachi, Tomoya, et al., "Simultaneous Separation, Metering, and Dilution of Plasma from Human Whole Blood in a Microfluidic System", *Analytical Chemistry*, 81(8), (2009), 3194-3198.

\* cited by examiner

MICROFLUIDIC SEPARATION OF PLASMA FOR COLORMETRIC ASSAY

RELATED APPLICATION

This application claims priority to U.S. Provisional Application Ser. No. 61/446,924 (entitled SEPARATION, QUANTIFICATION AND CONTINUOUS PREPARATION OF PLASMA FOR USE IN A COLORIMETRIC ASSAY IN A MICROFLUIDIC FORMAT, filed Feb. 25, 2011) which is incorporated herein by reference.

BACKGROUND

Providing desired amounts of blood plasma from whole human blood and subsequently preparing the sample for use in a colorimetric assay of blood constituents has been accomplished in prior devices by either using separate devices and processes to separate the plasma, or, has resulted in the need for larger blood samples due to inefficient use of larger blood samples.

In most prior systems, clinical chemistry analyzers do not extract plasma or serum from blood as a part of the analysis process. It is done separately; either at the time of collection from the patient by collecting blood in a serum or plasma tube, or by spinning whole blood (or plasma) in a centrifuge before loading the plasma into the clinical chemistry analyzer. However, one known system as part of the analysis process extracts plasma from whole blood by centrifugation, spinning the blood for 2.5 min.

There are no commercial products that extract plasma from a drop of blood (fingerstick, 20-30 µL of blood). The system using centrifugation requires 100 µL of blood, 3-4 times more volume than a fingerstick can normally supply.

Extraction of plasma from blood in other microfluidic formats are done by centrifugation, the use of micropillars, or the Zweifach-Fung bifurcation Law.

SUMMARY

A microfluidic method is used to separate a desired amount of plasma (a sample) from small amounts of whole human blood and subsequently prepare the sample for use in a colorimetric assay of blood constituents.

DETAILED DESCRIPTION

In the following description, reference is made to the accompanying drawings that form a part hereof, and in which is shown by way of illustration specific embodiments which may be practiced. These embodiments are described in sufficient detail to enable those skilled in the art to practice the embodiments, and it is to be understood that other embodiments may be utilized and that structural, logical and electrical changes may be made. The following description of example embodiments is, therefore, not to be taken in a limited sense, and the scope is defined by the appended claims.

Multiple embodiments are described that provide a single card or cartridge that operates to separate plasma from a blood sample, and provide the plasma to chambers that include a reagent to mix with the plasma and be subjected to colorimetric chemistry testing utilizing transmission of light through the testing chamber, or reflection of light from the chamber. Different cuvettes may be used as testing chambers. In some embodiments, the plasma may first be mixed with a diluent prior to mixing with the reagent. The card or cartridge in some embodiments provides the ability to properly fill each of one or more cuvettes, and to isolate the cuvettes from each other to avoid cross contamination of reagents.

Figure 1:
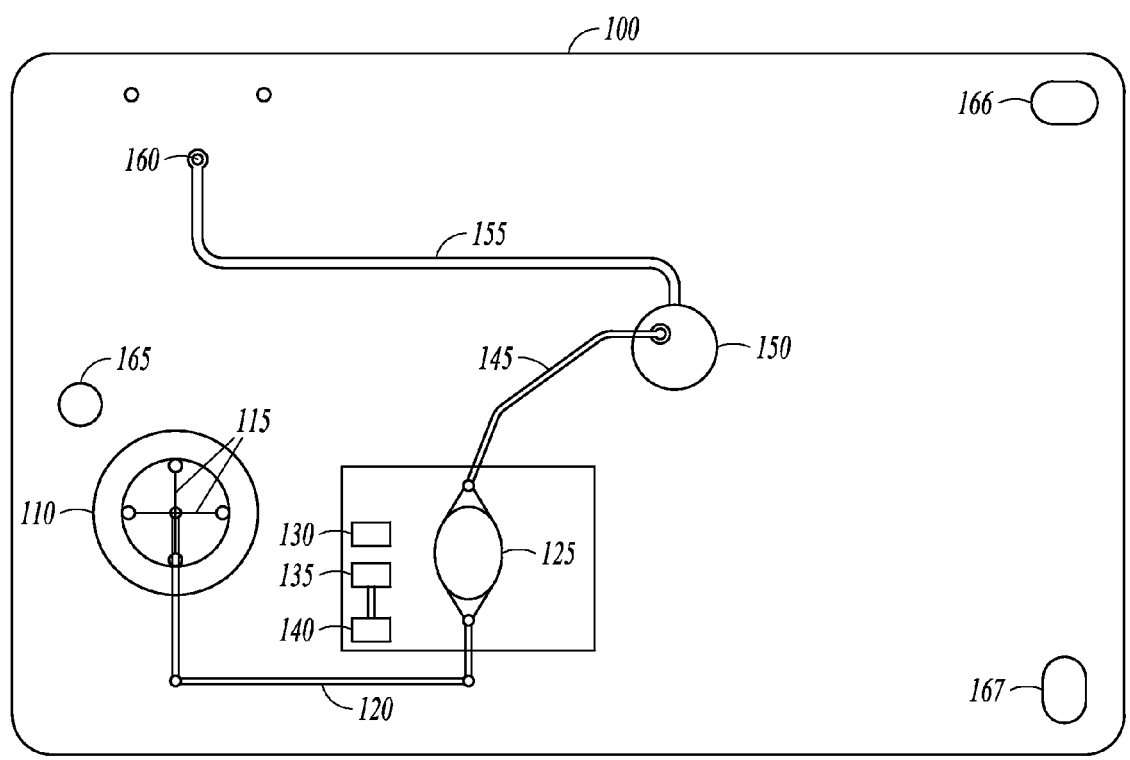
FIG. 1 is a schematic representation of a test cartridge according to an example embodiment.

A block schematic representation of a test cartridge 100 is illustrated in FIG. 1. In some embodiments, a plasma filter 110, referred to as a plasma separation membrane may be used to separate plasma from a blood sample. In one embodiment, the plasma filter may be a Pall Corporation Vivid™ plasma separation membrane. In further embodiments, a typical glass filter, Pall Corporation Cyto Membrane, etc), gas permeable membranes may be used to separate plasma from whole blood, which will then be prepared for determination of analyte concentration in one or more colorimetric clinical chemistry tests.

The plasma is collected in capillary collection channels 115 that are positioned opposite the filter 110 from the blood sample. The blood sample may be provided on top of the filter 110 such as from a finger prick, syringe, or other means of applying blood to the filter 110. The filter channels 115 are coupled to a channel 120 that transports the separated plasma to a test chamber, referred to as cuvette 125. Cuvette 125 is preloaded with a dry reagent in one embodiment that mixes with the plasma. The cuvette is then used to perform a colorimetric clinical chemistry test via a light source 130 and detector light detector 135. An output from the light detector 135 is provided to a controller 140 for analyte concentration analysis and communication off the cartridge 100. Details of the colorimetric clinical chemistry test are not provided as they are known to those of skill in the art. Note that in some embodiments, the light source 130 and light detector 135 may be positioned on the same side of the cuvette 125, with the cuvette 125 designed to reflect light back towards the light detector, such as by use of a reflective surface. In further embodiments, the light source and light detector may be positioned on opposite sides of the cuvette, such that light travels through the cuvette to the light detector.

In some embodiments, the light source, light detector, and controller may be positioned in a test device designed to accept the cartridge, which may be disposable. In such embodiments, the device may also provide the vacuum to provide force for moving the plasma through the various plumbing on the cartridge 100. The light source and detector may be positioned such that light is projected orthogonal to a surface of the cartridge on which the cuvettes are formed, with the cuvettes designed to reflect light back toward the light detector.

The cuvette 125 is also coupled via a channel 145 to a gas permeable membrane 150 that allows gas, but not plasma to pass. The membrane 150 is coupled via a gas channel 155 to a vacuum port 160. The vacuum port 160 provides a vacuum to cause the plasma to separate from the blood at plasma filter 110 and to travel through the various channels and fill cuvette 125 with plasma. The channels are adapted to hold a small volume of plasma compared to the volume of the cuvette 125 in one embodiment. The plasma stops flowing when it reaches membrane 150, allowing the use of a well quantified plasma sample to be provided to cuvette 125 for testing without the need for significant surplus amounts of plasma being separated such that small blood samples may be used.

In one embodiment, the area under the plasma filter 100 contains a capillary channel 115 with dimensions that will allow quick and easy fill of plasma. In one embodiment, horizontal channel heights are 0.002" to 0.003" tall or, if taller, may contain a pattern of lines underneath with vertically oriented capillary channels for extracting plasma.

In some embodiments, the cartridge 100 is designed to be positioned in a certain orientation to facilitate the separation of plasma from blood with an assist from gravity. While the vacuum may provide most of the force, the cartridge 100 may be positioned to assist with gravity.

The flow of blood into and plasma out of the filter 110 occurs in a transverse direction as indicated by capillary collection channels 115, to facilitate easy production of plasma. In one embodiment, the filter sits above (and centered over) a the capillary channel. A typical gap between the bottom of the plasma filter 110 and the top of the collection channel 115 is between 2 and 4 mils). A vacuum is applied to the capillary channel underneath the filter to start the flow of plasma through the filter, leaving the blood cells trapped in the filter matrix. The vacuum may be provided via vacuum port 160 or a separate source of vacuum in different embodiments. Flow of plasma through the filter 110 can also be generated by applying pressure on the blood on top of the filter 110 In one embodiment, the outer perimeter of the filter is sealed by compression of the top and bottom surfaces to prevent blood from leaking around the edge and allowing cells to enter the plasma.

Various embodiments may provide a separation membrane in a microfluidic blood constituents assay cartridge that is used to produce small amounts of high quality plasma from whole blood. A vacuum may be used to create a flow of plasma through the separation membrane in a microfluidic blood constituents assay cartridge.

In a further embodiment, cartridge 100 includes one or more registration features as indicated at 165, 166, and 167 dispersed at various locations. The registration features may simply be holes in a card or substrate on which the microfluidics are supported. In further embodiments, the registration features may include grooves or any combination of different structures designed to align the cartridge 100 into a testing device. The features 165, 166, and 167 ensure that when the cartridge 100 is inserted into the testing device, it is positioned precisely with components that interface with the cartridge 110, such as vacuum ports and sensing devices to perform tests on the plasma in the cuvettes.

Figure 2:
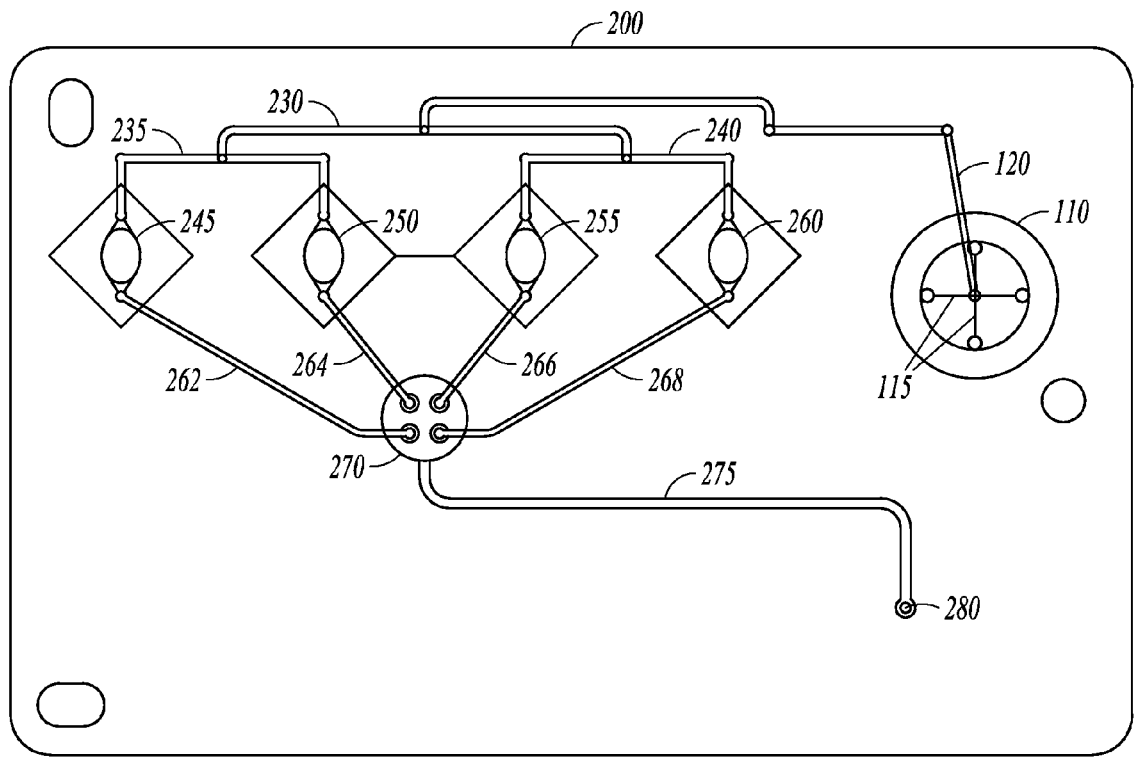
FIG. 2 is a schematic representation of a test cartridge for preparing multiple interrogation cuvettes according to an example embodiment.

FIG. 2 is a schematic diagram of a cartridge 200 includes a filter 110 and collection channels 115 as described in FIG. 1 wherein the numbering of like components is consistent. The separated plasma is provided via channel 120 to a distribution channel 230. The distribution channel is split into two further distribution cross channels 235 and 240 that are each coupled to respective pairs of cuvettes 245, 250 and 255, 260. The cuvettes may each have a different dry reagent for mixing with the plasma as they fill. Each cuvette has an exit channel 263, 264, 266, and 268 that are coupled to a gas permeable membrane 170 and discharge channel 275. Discharge channel 275 in one embodiment is coupled to a vacuum port 280 to provide force for moving the plasma through the channels and to fill the cuvettes, making them ready for testing. Since the cuvettes are separated by the length of each cross channel, there is very little if any cross contamination of reagent between cuvettes.

Figure 3:
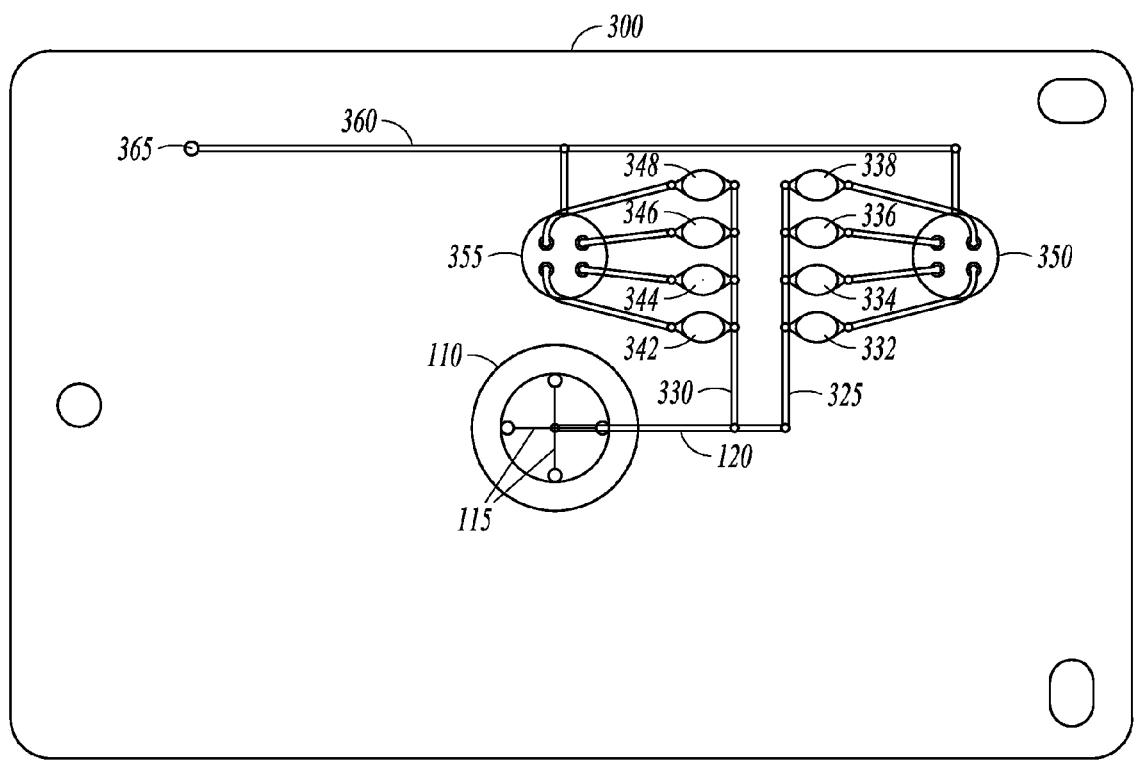
FIG. 3 is a schematic representation of a test cartridge for sequentially filling multiple interrogation cuvettes according to an example embodiment.

FIG. 3 is a schematic diagram of a cartridge 300 includes a filter 110 and collection channels 115 as described in FIG. 1, wherein the numbering of like components is consistent. The separated plasma is provided via channel 120 to a pair of distribution channels 325, 330. The distribution channels each coupled to respective sets of cuvettes 332, 334, 336, 338, and 342, 344, 346, and 348. The cuvettes may each have a different dry reagent for mixing with the plasma as they fill. Each cuvette has an exit channel that is coupled to a gas permeable membranes 350 and 355 and a discharge channel 360. Discharge channel 360 in one embodiment is coupled to a vacuum port 365 to provide force for moving the plasma through the channels and to fill the cuvettes, making them ready for testing. The cuvettes on each distribution channel are arranged in sequence along the respective distribution channel and coupled to the channels in a manner that results in reduced impedance to liquid than the corresponding channels. Thus, the cuvettes fill in sequence, and little cross contamination between cuvettes occurs. In both cartridges 200 and 300, the number of cross channels and cuvettes per cross channel may be varied as desired.

Figure 4:
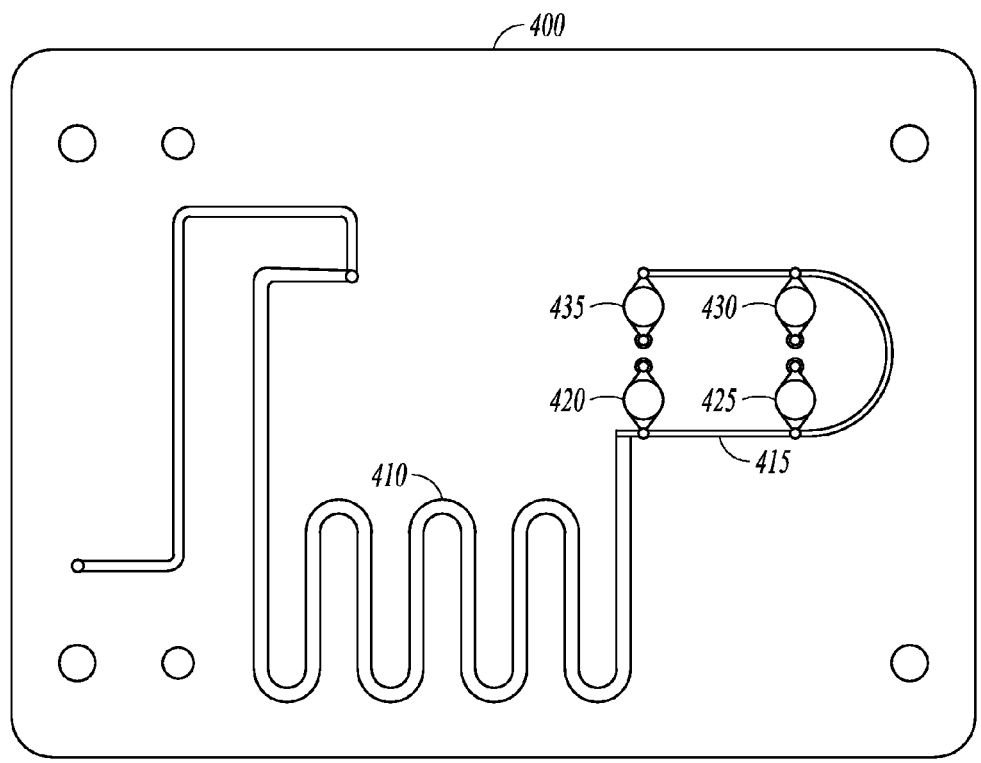
FIG. 4 is a schematic representation of an alternative test cartridge for sequentially filling multiple interrogation cuvettes according to an example embodiment.
Figure 5:
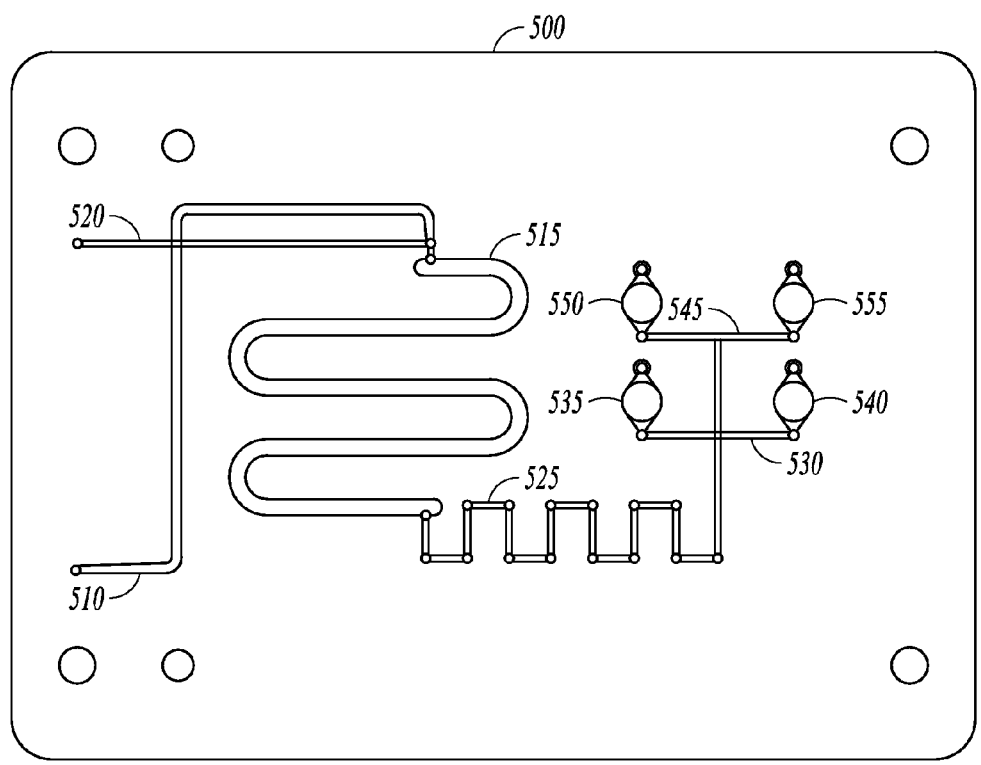
FIG. 5 is a schematic representation of a further alternative test cartridge for sequentially filling multiple interrogation cuvettes according to an example embodiment.

FIGS. 4 and 5 block schematic diagrams that illustrate cartridges at 400 and 500 respectively that facilitate sequential filling of cuvettes. While sources of air at either a higher or lower than ambient air pressure (positive or negative) may be used to push fluids in the channels, bellows or pumps may also be used in further embodiments. The cuvettes may include reagents to mix with plasma and may be positioned to receive light for testing.

In FIG. 4, a channel 410 is coupled to a source of plasma and a locomotive source of air to push plasma through the channel 410 to a smaller channel 415 along which a sequence of four cuvettes 420, 425, 430, and 435 is coupled. The cuvettes each have a lower impedance to liquid than the smaller channel. Since the smaller channel 415 presents a larger impedance than the openings to the cuvettes, each cuvette fills in a desired sequence. Channel 415 may also be coupled to a gas permeable membrane as shown in prior embodiments to facilitate the flow of plasma to the cuvettes.

In FIG. 5, a channel 510 is coupled to a source of plasma and a locomotive source of air to push plasma through the channel to a mixing channel 515. Mixing channel 515 is coupled to a diluent channel 520 to provide diluent to the mixing channel to mix with the plasma. The mixing channel in one embodiment serpentines along the cartridge 500 in order to provide suitable distance for properly mixing the diluent and plasma. In some embodiments, the air may be used to move the diluent and plasma back and forth in the mixing channel to facilitate mixing. In further embodiments, the flow of the diluent and plasma together through a length of the mixing channel 520 provide for suitable mixing. The fluid flow may be reduced while initiating mixing, but may then be increased over time as more plasma and diluent are introduced from the channels 510 and 520.

Following mixing, the plasma and diluent are provided to a cuvette distribution channel 525, which may also serpentine to facilitate further mixing. The distribution channel 525 has a smaller cross section than the mixing channel, and does not contain a large volume of fluid. A first cross channel 530 is coupled to the distribution channel and is also coupled to two cuvettes 535 and 540. These cuvettes present a lower impedance to liquid than the cross channel and distribution channel 530, and thus fill prior to significant amounts of liquid travel past the cross channel 530. A second cross channel 545 is coupled to two further cuvettes 550 and 555. These cuvettes fill after cuvettes 535 and 540. The channels provide for isolation of the cuvettes from each other such that each may contain a different reagent and not contaminate other cuvettes, ensuring integrity of the tests that may be performed on the plasma, diluent, and reagent in each cuvette. In further embodiments, more cuvettes may be located on each cross channel, and further cross channels may be provided.

In one embodiment, the mixing channel 515 is sized to provide an amount of plasma and diluent mixture to fill the cuvettes, without excess mixture. Thus, the mixture is well quantitated, and small amounts of blood may be used for the testing. The distribution channel may also continue to a gas permeable membrane which is not shown. The volume of the distribution channel following the last cuvette may be large enough to hold all excess mixture such that the cross channels contain no mixture. This effectively further isolates each cuvette from each other.

Figure 6:
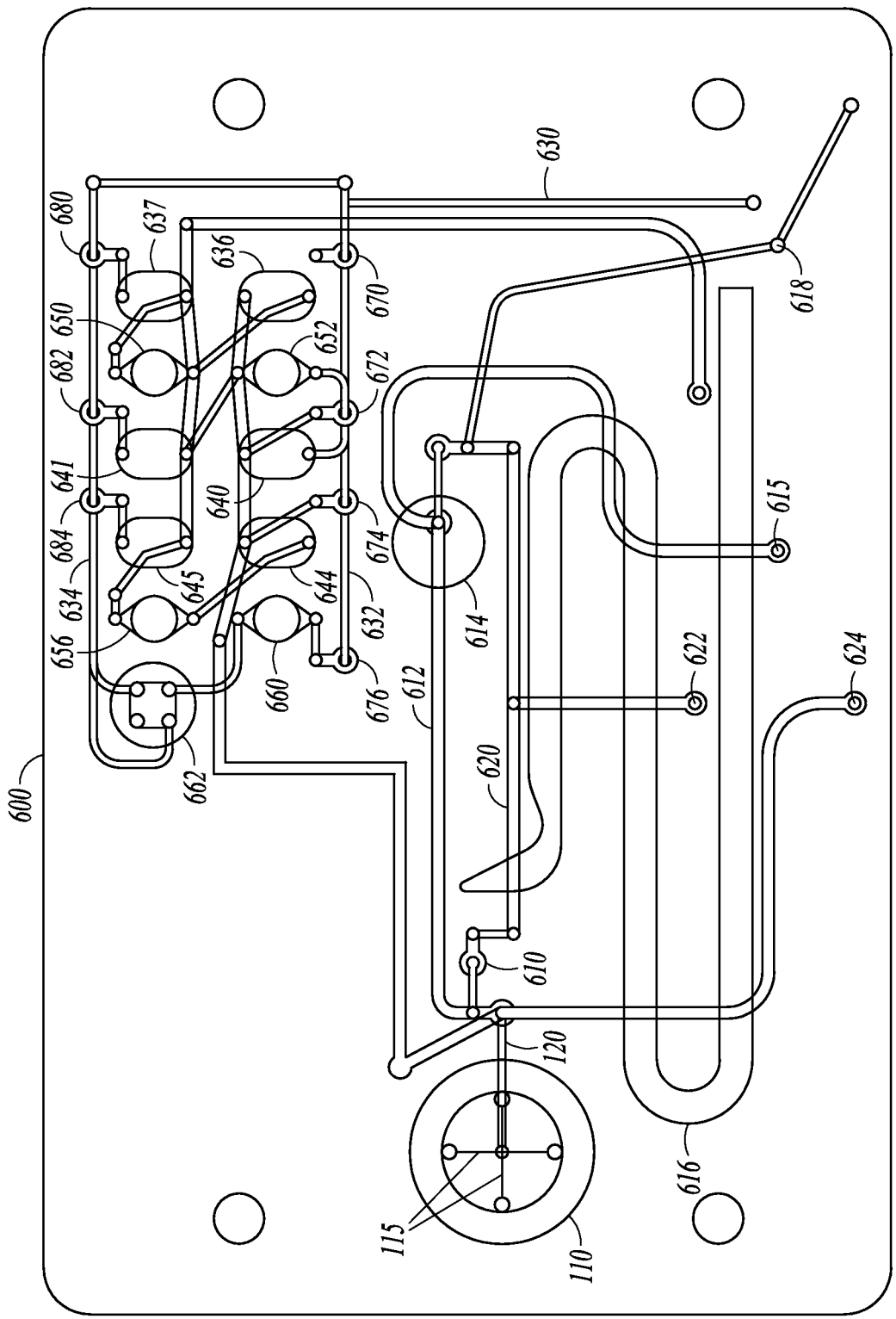
FIG. 6 is a schematic representation of an alternative test cartridge for preparing multiple interrogation cuvettes with a measured plasma and diluent mixture along with reagent according to an example embodiment.

FIG. 6 is a block schematic diagram illustrating a cartridge 600 that includes a filter 110 and collection channels 115 as described in FIG. 1 wherein the numbering of like components is consistent. The separated plasma is provided to a channel 120 that is coupled to a mixer valve 610.

In some embodiments, the filter 110 may be a typical glass filter, Pall Corporation Cyto Membrane, etc., gas permeable membranes that may be used to separate plasma from whole blood. Valve 610 is first set to couple a plasma quantitation channel 612 that has a desired volume calculated to provide a desired volume of plasma. One end of the quantitation channel 612 is coupled via a gas permeable membrane 614 to an air port 615 that allows the channel 612 to fill completely. The quantitation channel 612 provides a defined-volume channel, i.e. a channel between a valve and a gas permeable membrane, to quantitate the plasma sample in a microfluidic blood constituents assay cartridge. A further valve 617 may be coupled to the quantitation channel 612 to couple the quantitation channel to an air inlet and diluent inlet 618.

In one embodiment, once the plasma is quantitated via channel 612, the mixer valve 612 then couples the plasma to a mixing channel 616. The diluent inlet 618 is also coupled to the mixing channel 616 via a diluent channel 620, again, via the mixer valve 610. An additional air port 622 is coupled to the diluent channel 620, and a further air port is coupled to the channel 120 to facilitate an oscillatory fluid motion in the mixing channel 616 to create a homogenous mixture of diluted plasma as a second step in the sample preparation process. In one embodiment, the oscillatory motion helps to create a single homogeneous bolus of fluid even though the plasma and diluent are introduced sequentially to the mixing channel. The homogeneity of the fluid is created by moving the single plasma/diluent bolus of fluid back and forth in the mixing channel (channel height approximately 0.7 mm×width of 2 mm, for example). By repeatedly moving the fluid from one end of the channel to the other, the downstream diluent-rich portion of the fluid bolus is brought into contact with the initially plasma-rich portion of the fluid, continually mixing the fluids by the shear strain of the fluid that is induced by laminar flow.

In some embodiments, the initial flow of fluid in the mixing channel 616 may be fairly slow, with introduction of the plasma occurring first, and a larger quantity of diluents following. The slow flow of fluid initially facilitates mixing of the diluent and plasma without the need for oscillatory motion. Once mixing starts, the flow may be increased without degradation of the mixing.

Once mixed, the plasma and diluent solution is provided to multiple cuvettes via a channel 630 along with multiple valves and bellows.

Channel 630 is bifurcated into two distribution channels 632 and 634. The distribution channels 632 and 634 are each coupled to three pairs of bellows 636 and 637, 640 and 641, and 644 and 645. At least one bellow in each pair of bellows contains a reagent, and are coupled via a series of valves on the distribution channels to respective interrogation cuvettes 650, 652, and 656.

A fourth cuvette 660 is coupled between distribution channel 632 and a gas permeable membrane 662, and serves as a calibration mechanism for the other cuvettes. It may be read by test equipment when empty to account for potential scratches and tolerances in a manufacturing process used to make the cartridge 600. To some extent, all the cuvettes may be made at the same time and exhibit similar deviations from nominal. Measurements may be made both when empty and when filled with the mixture as desired.

As mentioned previously, the distribution channels contain a series of valves that may be actuated to fill the bellows and the corresponding cuvettes. Distribution channel 632 contains valves 670, 672, 674, and 676 positioned to operate in conjunction with valves 680, 682, and 684 on distribution channel 634 in order to fill the bellows, mix the diluent and plasma with the reagent, and fill the cuvettes. Control of the valves and bellows may be done under the control of a testing device into which the cartridge is inserted. The bellows may be pneumatically or mechanically actuated bellows to implement oscillating flow in a mixing channel in a microfluidic blood constituents assay cartridge.

The same shearing motion is also used to mix the diluted plasma with a solid reagent in the interrogation cuvettes. Pumps, such as bellows are actuated to propel the diluted plasma back and forth between cuvette and reagent chamber in conjunction with the valves, until a homogeneous fluid is created.

One potential advantage of some embodiments for a colorimetric assay of blood constituents is sequential filling and fluidic isolation of multiple cuvettes. This sequential fill occurs by locating the cuvettes serially in a fluidic circuit as illustrated in FIGS. 3-6. To enable the fluid to displace the air already in the cuvettes, they may be individually vented through a gas permeable membrane. When the first cuvette is full, the fluid proceeds to the next cuvette, filling that cuvette before travelling to the next (and so on). As the last of the liquid solution (followed by air) travels past a full cuvette, the liquid is bifurcated, leaving the full cuvette fluidically isolated from the rest of the cuvettes. In FIG. 6, the last of the fluid proceeds to the final cuvette 660. Interrogation of this cuvette determines if there are any abnormalities of the diluted plasma sample and if all the cuvettes have been filled.

Gas permeable membrane (gpm) and valves are typically used in microfluidic cards. In some embodiments, a combination of all three serves to quantitate plasma in a clinical chemistry analyzer.

In various embodiments, a microfluidic cartridge design extracts plasma from whole blood, quantitates the plasma, mixes a diluent and plasma to create a homogenous liquid bolus, fills multiple interrogation cuvettes sequentially until all cuvettes are full, and fluidically isolates each cuvette.

In addition, the last cuvette may be used to determine whether or not there was sufficient sample to fill all cuvettes and analyze sample integrity (lipemia, icteria, and hemolysis). A single (elastomeric) layer on the card contains cavities to hold the gas permeable filter and plasma membrane and be used for all valves and bellows required to move fluid through the card.

In order to minimize the number of I/O ports required while ensuring extensibility of the design for future panels, the cuvette valves and bellows can be operated from a same I/O port. Flow of fluids through the circuits is controlled with the use of on card-valves and gas permeable membranes. As the fluid process occurs, each cuvette may be calibrated with the LEDs that are used for analyte detection in that particular cuvette.

In operation, plasma may be pulled into the quantitation chamber up to a gas permeable membrane. A valve may be used to prevent the plasma from going into the mixing channel. The mixing channel valve is opened and the plasma filter valve is closed to segregate the filter from the quantitation chamber; a precise amount of diluent is added to the plasma channel and the fluid bolus is pushed into the mixing channel.

The plasma and diluent are mixed by pneumatically moving the fluid bolus back and forth in the mixing channel by alternating the pressure gradient until the diluted plasma is homogenous. This solution is then pneumatically moved into a fluidic network that connects the mixing channel to the cuvettes.

The diluted plasma is moved by air pressure to fill the first cuvette and its reagent chamber and then to press against a gas permeable membrane that stops the flow in this branch of the fluidic network. Still under air pressure, the fluid proceeds to the next cuvette and fills that up before travelling to the next. As the rear of the fluid front travels past a full cuvette, the fluid is bifurcated, leaving the full cuvette isolated from the rest.

The diluted plasma and reagent in each cuvette and its reagent chamber may be mixed by actuating the bellows in the reagent chamber to cause fluid flow back and forth between cuvette and reagent chamber. Once mixed, the prepared sample fills each analysis cuvette and each cuvette may be interrogated in series or in any order desired.

Use of a defined-volume channel, i.e. the channel between a valve and a gas permeable membrane, acts to quantitate the plasma sample in a colorimetric card. Use of on-card valves for isolating the plasma filter as part of plasma quantitation.

In one embodiment, the edge of filter is sealed around the perimeter on top and bottom. The design height of the filter cavity relative to the thickness of the filter as the filter may be determined to help form a compressive seal around the perimeter to prevent leakage of the blood sample around the filter. In one embodiment, the current dimensions, for example, provide a 0.012" cavity height to contain a 0.0129" thick filter.

A smoothly-varying vacuum applied under the plasma filter is helpful to prevent RBC lysis. Sufficient air exchange above the plasma filter allows displacement of air in the filter by blood and extraction of plasma.

In one embodiment, the following method is used. Plasma is separated from whole blood through the separation membrane. The Plasma is then quantitated in the quantitation channel.

Diluent is subsequently added to the card through into the plasma quantitation channel, pushing the plasma out of the capillary channel into a larger "mixing" channel. When the diluent and plasma are completely out of the quantitation channel and into the larger mixing channel, the fluids are then pushed back and forth until completely mixed. This diluted plasma is then pushed into the cuvettes/reagent chambers. Alternatively, the mixing occurs without oscillating the fluid, but by slowly starting the flow of fluids and gradually increasing the rate to a desired rate.

After each individual reagent chamber is filled, the bellows are actuated to move the diluted plasma and reagent back and forth between the reagent chamber and cuvette until they are completely mixed. In one embodiment, there are two reagent chambers for each cuvette, so the fluid is moved back and forth from reagent chamber to reagent chamber.

While a bellows or pumps are described as propulsion methods to push fluids back and forth in the mixing channel and between cuvettes and reagent chambers, in further embodiments, sources of air at either a higher or lower than ambient air pressure (positive or negative) may be used to push fluids.

In one embodiment, the card or cartridge has multiple layers, so channels can cross over each other without interacting. The pairs of bellows (on either side of a cuvette) are used to mix the reagent into the fluid in the cuvette. The mixing of diluent and plasma in the mixing channel is done by push/pull oscillation of the liquid by air pressure which may be provided by a pump or source of air at either a higher or lower than ambient air pressure. In further embodiments, such actuation may be provided by additional bellows.

Examples

1. A device comprising:
   a plasma separation membrane;
   a capillary channel positioned adjacent to the plasma separation membrane to receive plasma from blood placed on the plasma separation membrane;
   at least one cuvette coupled to the capillary channel;
   a gas permeable membrane; and
   a distribution channel coupled to the capillary channel to provide plasma to the cuvette, wherein the cuvette is configured to hold an amount of plasma with reagent suitable for colorimetric assay by a tester to hold the device.

2. The device of example 1 wherein the plasma separation membrane sits above the capillary channel.

3. The device of example 2 and further comprising a port to couple a source of air to the capillary channel to create a differential pressure across the plasma separation membrane.

4. The device of example 3 wherein the source of air comprises negative pressure applied to the capillary channel such that plasma flows through the plasma separation membrane leaving blood cells trapped in the plasma separation membrane.

5. The device of example 4 and further comprising a mixing channel coupled to the capillary channel and a source of air to move fluid back and forth in the mixing channel to mix the plasma with a diluent.

6. The device of example 5 wherein the source of air comprises air at positive and negative pressures.

7. The device of example 6 wherein the source of air includes a pump or bellows.

8. The device of example 5 or 6 wherein the gas permeable membrane is sequentially coupled to multiple cuvettes to facilitate sequential filling of the cuvettes.

9. A cartridge comprising:
   a plasma separation membrane;
   a capillary channel positioned adjacent to the plasma separation membrane to receive plasma from blood placed on the plasma separation membrane;
   a quantitation channel coupled to the capillary channel to provide a selected quantity of plasma;
   a mixing channel coupled to the quantitation channel and a source of diluent to mix the selected quantity of plasma with diluent;

at least one interrogation cuvette coupled to the mixing channel to receive the mixed plasma and diluent; and a gas permeable membrane coupled to the cuvette to facilitate flow of the mixed plasma and diluent into the cuvette.

10. The cartridge of example 9 and further comprising:
multiple cuvettes coupled to the mixing channel via at least one distribution channel;
multiple valves coupled to at least one distribution channel to controllably couple the cuvettes to receive the mixed plasma and diluent; and
multiple bellows containing reagent coupled to at least one distribution channel and cuvettes to mix the reagent with the mixed plasma and diluent, wherein the cuvette is configured to hold an amount of plasma with reagent suitable for colorimetric assay by a tester to hold the device.

11. The cartridge of example 10 wherein the bellows, valves, and cuvettes are configured to provide oscillation of fluid between multiple pairs of bellows, each pair coupled to a corresponding cuvette, to provide the mixture of reagent, plasma and diluent to the corresponding cuvettes and to provide isolation of the cuvettes from each other.

12. The cartridge of example 11 and further comprising at least one port to provide an air pressure difference to move the plasma and diluent through the channels.

13. The cartridge of example 12 wherein the air pressure difference is a vacuum.

14. The cartridge of any of examples 9-13 wherein the elements are support on a card having at least one registration feature to align the card in a colorimetric assay test fixture.

15. A method comprising:
filtering blood cells from blood to obtain plasma in a microfluidic channel;
moving the plasma through a distribution channel coupled to the microfluidic channel;
filling at least one interrogation cuvette with plasma and a reagent; and
using a gas permeable membrane to facilitate filling and isolation of the at least one cuvette via the distribution channel.

16. The method of example 15 and further comprising adding a diluent to a mixing channel coupled to the microfluidic channel;
moving the plasma and diluent back and forth within the mixing channel to mix them together; and
providing the mixed plasma and diluents to the distribution channel.

17. The method of example 16 and further comprising providing the plasma to a plasma quantitation channel to define a fixed amount of plasma to add to the mixing channel.

18. The method of any of examples 15-17 wherein multiple cuvettes are filled sequentially.

19. The method of example 18 wherein each cuvette is filled until all gas in the cuvette is removed through the gas permeable membrane, whereupon the next sequential cuvette is filled.

20. The method of example 19 wherein air is used to isolate filled cuvettes from each other.

Although a few embodiments have been described in detail above, other modifications are possible. For example, the logic flows depicted in the figures do not require the particular order shown, or sequential order, to achieve desirable results. Other steps may be provided, or steps may be eliminated, from the described flows, and other components may be added to, or removed from, the described systems. Other embodiments may be within the scope of the following claims.

The invention claimed is:

1. A device comprising:
a plasma separation membrane disposed in a first layer of the device;
multiple collection capillaries positioned in a second layer of the device beneath and adjacent to the plasma separation membrane to extract plasma from blood placed on the plasma separation membrane;
at least one cuvette coupled to the capillary collection channels;
a gas permeable membrane; and
a distribution channel coupled to the capillary collection channels to provide plasma to the cuvette, wherein the cuvette is configured to hold an amount of plasma with reagent suitable for colorimetric assay by a tester to hold the device.

2. The device of claim 1 wherein the multiple capillary collection channels are positioned beneath the plasma separation membrane.

3. The device of claim 2 and further comprising a port to couple a source of air to the capillary channel to create a differential pressure across the plasma separation membrane and wherein the capillary channels are vertically oriented with respect to the membrane to extract plasma from the membrane.

4. The device of claim 3 wherein the source of air comprises negative pressure applied to the capillary channel such that plasma flows through the plasma separation membrane leaving blood cells trapped in the plasma separation membrane.

5. The device of claim 4 and further comprising a serpentine mixing channel coupled to the capillary channel and the source of air to move fluid back and forth in the mixing channel to mix the plasma with a diluent.

6. The device of claim 5 wherein the source of air comprises air at positive and negative pressures.

7. The device of claim 6 wherein the source of air includes a pump or bellows.

8. The device of claim 5 wherein the gas permeable membrane is sequentially coupled to multiple cuvettes to facilitate sequential filling of the cuvettes.

9. A cartridge comprising:
a plasma separation membrane;
multiple capillary collection channels positioned adjacent to the plasma separation membrane to receive plasma from blood placed on the plasma separation membrane;
a quantitation channel coupled to the capillary channels to provide a selected quantity of plasma;
a mixing channel coupled to the quantitation channel and a source of diluent to mix the selected quantity of plasma with diluent;
at least one interrogation cuvette coupled to the mixing channel to receive the mixed plasma and diluent; and
a gas permeable membrane coupled to the cuvette to facilitate flow of the mixed plasma and diluent into the cuvette.

10. The cartridge of claim 9 and further comprising:
multiple cuvettes coupled to the mixing channel via at least one distribution channel;
multiple valves coupled to at least one distribution channel to controllably couple the cuvettes to receive the mixed plasma and diluent; and
multiple bellows containing reagent coupled to at least one distribution channel and cuvettes to mix the reagent with the mixed plasma and diluent, wherein the cuvette is configured to hold an amount of plasma with reagent suitable for colorimetric assay by a tester to hold the device.

11. The cartridge of claim 10 wherein the bellows, valves, and cuvettes are configured to provide oscillation of fluid between multiple pairs of bellows, each pair coupled to a corresponding cuvette, to provide the mixture of reagent, plasma and diluent to the corresponding cuvettes and to provide isolation of the cuvettes from each other.

12. The cartridge of claim 11 and further comprising at least one port to provide an air pressure difference to move the plasma and diluent through the channels.

13. The cartridge of claim 12 wherein the air pressure difference is a vacuum.

14. The cartridge of claim 9 wherein the elements are supported on a card having at least one registration feature to align the card in a colorimetric assay test fixture.

15. A method comprising:
filtering blood cells from blood to obtain plasma in multiple collection capillaries of a microfluidic channel using a filter disposed in a filter layer of a multilayer card, wherein the collection capillaries are disposed in a distribution layer positioned beneath the filter layer of the multilayer card;
moving the plasma through a distribution channel in the distribution layer coupled to the microfluidic channel;
filling at least one interrogation cuvette with plasma and a reagent; and
using a gas permeable membrane to facilitate filling and isolation of the at least one cuvette via the distribution channel.

16. The method of claim 15 and further comprising
adding a diluent to a serpentine mixing channel coupled to the microfluidic channel;
moving the plasma and diluent back and forth within the mixing channel to mix them together; and
providing the mixed plasma and diluents to the distribution channel wherein the distribution channel has a smaller cross section than the mixing channel.

17. The method of claim 16 and further comprising providing the plasma to a plasma quantitation channel to define a fixed amount of plasma to add to the mixing channel.

18. The method of claim 15 wherein multiple cuvettes are filled sequentially.

19. The method of claim 18 wherein each cuvette is filled until all gas in the cuvette is removed through the gas permeable membrane, whereupon the next sequential cuvette is filled.

20. The method of claim 19 wherein air is used to isolate filled cuvettes from each other.

* * * * *